US008337754B2

(12) United States Patent  (10) Patent No.: US 8,337,754 B2
Emery et al.  (45) Date of Patent: Dec. 25, 2012

(54) AUTOMATED DEVELOPER FOR IMMUNO-STAINED BIOLOGICAL SAMPLES

(75) Inventors: Michael P. Emery, Santee, CA (US); Matthew C. Wallace, Carlsbad, CA (US); James E. Sinclair, Carlsbad, CA (US); Raymond J. Gonzales, Chula Vista, CA (US); Brian Grot, San Diego, CA (US); Sanjay S. Magavi, Cambridge, MA (US)

(73) Assignee: Vertex Pharmaceuticals, Incorporated, Cambridge, MA (US)

( * ) Notice: Subject to any disclaimer, the term of this patent is extended or adjusted under 35 U.S.C. 154(b) by 282 days.

(21) Appl. No.: 12/644,839

(22) Filed: Dec. 22, 2009

(65) Prior Publication Data

US 2011/0151482 A1  Jun. 23, 2011

(51) Int. Cl.
 *G01N 21/00* (2006.01)
(52) U.S. Cl. ............... 422/65; 422/63; 422/64; 422/500
(58) Field of Classification Search .................... 422/50, 422/500–502, 63–65
 See application file for complete search history.

(56) References Cited

U.S. PATENT DOCUMENTS

| | | | |
|---|---|---|---|
| 3,533,744 A | 10/1970 | Unger | |
| 3,831,903 A * | 8/1974 | Harmel, Jr. | ................... 366/145 |
| 4,199,013 A | 4/1980 | Reich et al. | |
| 4,859,419 A | 8/1989 | Marks et al. | |
| 5,023,187 A | 6/1991 | Koebler et al. | |
| 5,287,758 A | 2/1994 | Geiss et al. | |
| 5,496,473 A * | 3/1996 | Chow | .............................. 210/635 |
| 5,817,954 A | 10/1998 | Kahng et al. | |
| 6,192,945 B1 | 2/2001 | Ford et al. | |
| 2001/0003652 A1 | 6/2001 | Freeman | |
| 2005/0032199 A1 * | 2/2005 | Takahashi | .................. 435/286.5 |
| 2005/0153453 A1 | 7/2005 | Copeland et al. | |
| 2008/0233653 A1 | 9/2008 | Hess et al. | |

FOREIGN PATENT DOCUMENTS

EP  1 710 587 A2  10/2006

OTHER PUBLICATIONS

HTTP://www1.gelifesciences.com/aptrix/upp01077.nsf.content/western_blot_site~labelling~ . . . , GE Health Life Sciences "Processor Plus" two pgs.
PCT, International Preliminary Report on Patentability dated Jun. 26, 2012 for International Application No. PCT/US2010/059728.
Stark, Erwin et al., An Automated Device for Immunocytochemistry, Journal of Immunological Methods, 1988, pp. 89-92, vol. 107, Elsevier Science Publishers B.V.
PCT, International Search Report and the Written Opinion, dated Apr. 19, 2011, for International Application No. PCT/US2010/059728.

* cited by examiner

*Primary Examiner* — Jyoti Nagpaul
(74) *Attorney, Agent, or Firm* — Knobbe Martens Olson & Bear LLP

(57) ABSTRACT

Disclosed herein are systems and methods for the developing of immuno-stained biological samples. The systems disclosed herein are automated and are configured to control one or more steps of the developing procedure. Reagents may be added using automatic syringe dispensing. Reagent temperature, reagent stirring, and wash procedures are programmable and can be separately controlled for separate immuno-staining procedures that are performed at the same time.

19 Claims, 6 Drawing Sheets

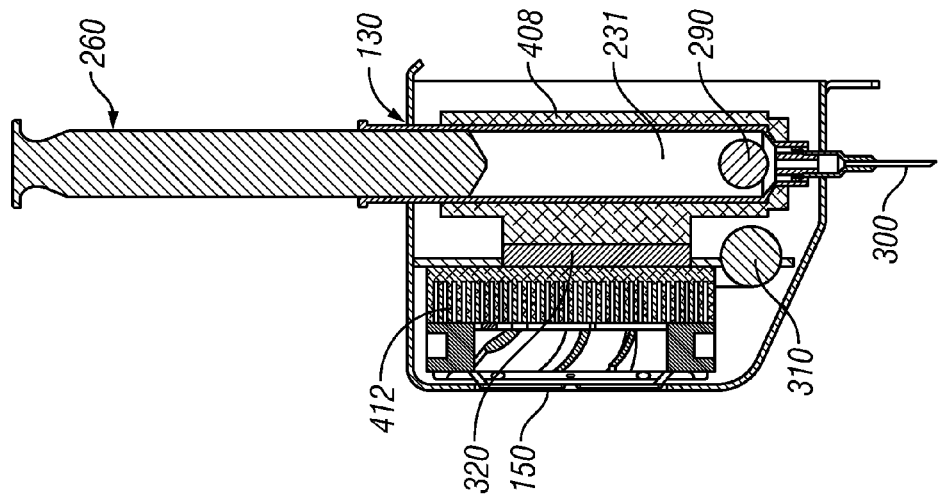
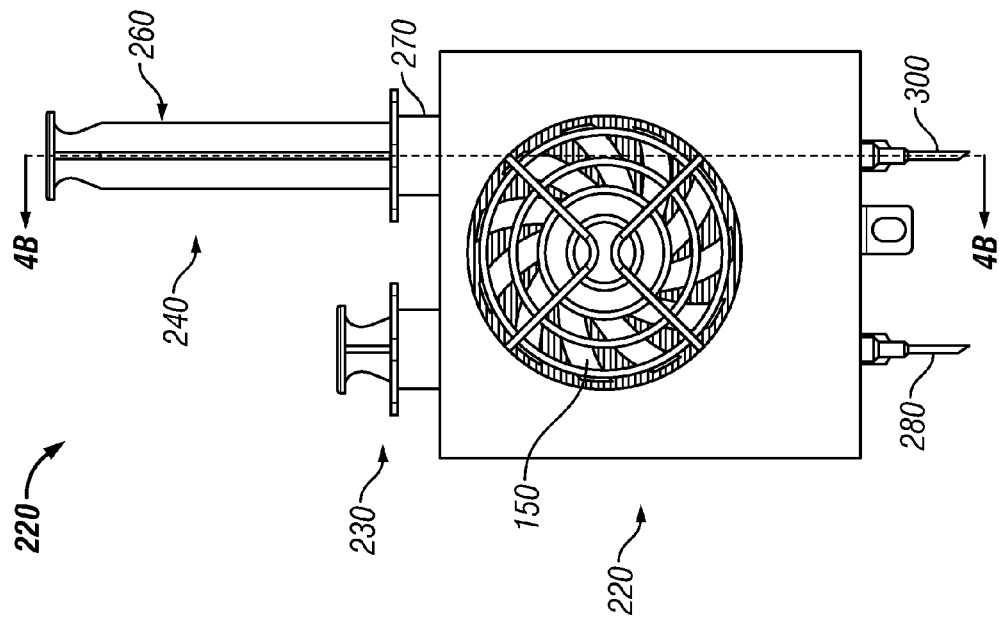
FIG. 4B
FIG. 4A

AUTOMATED DEVELOPER FOR IMMUNO-STAINED BIOLOGICAL SAMPLES

BACKGROUND OF THE INVENTION

1. Technical Field

The embodiments disclosed herein relate to automated systems for processing blots used in the field of molecular biology.

2. Introduction

Western blotting is one example of an immunostaining technique used extensively for over 30 years in biology laboratories, in order to detect one or more target proteins in a sample. A schematic of the Western blot procedure is shown in FIG. 1. First, the sample is loaded onto a gel and the proteins are electrophoretically separated in the gel, e.g., an SDS-PAGE gel, or a non-denaturing gel. (FIG. 1, step 1). The protein(s) within the gel are transferred, or blotted, onto filter paper or other membrane, either by capillary forces, or by electrophoresis, or blotted onto a piece of filter paper, e.g., polyvinylidene difluoride (PVDF) or nitrocellulose (FIG. 1, step 2). Protein binding to the filter is based upon hydrophobic interactions, as well as charged interactions between the membrane and protein. As such, the filter paper possesses non-specific protein binding properties in that it generally binds all proteins substantially equally.

After transfer, the filter paper is treated, or blocked, to prevent non-specific binding of proteins at subsequent steps. Blocking of non-specific binding is achieved by placing the membrane in a dilute solution of protein, such as bovine serum albumin or non-fat dry milk. The protein in the dilute solution attaches to the membrane in all places where the target proteins have not attached. Thus, when the antibody is added, there is no room on the membrane for it to attach other than on the binding sites of the specific target protein. This reduces "noise" in the final product of the Western blot, leading to clearer results, and eliminates false positives.

The detection of the target protein(s) is achieved either in a one-step or two-step process. In the two-step process, the blocked filter is treated with a primary antibody specific to the target protein, followed by treatment with a secondary antibody specific for the primary antibody, and which includes a detectable moiety. A dilute solution of primary antibody (generally between 0.5 and 5 µg/mL) is incubated with the membrane under gentle agitation. The antibody solution and the membrane are incubated together for anywhere from 30 minutes to overnight. It can also be incubated at different temperatures, with warmer temperatures being associated with more binding, both specific (to the target protein, the "signal") and non-specific ("noise").

The membrane is rinsed or washed to remove unbound primary antibody, and then incubated with a secondary antibody specific for the primary antibody and that contains a detectable moiety, which can be detected, as an indicator of the presence and/or amount of target proteins present in the original gel. The secondary antibody is incubated with the membrane for a period of time, with gentle agitation.

Alternatively, in the one-step process, the blocked membrane can be incubated with a primary antibody that contains a detectable moiety, thereby eliminating the necessity for a secondary antibody.

Treatment of the blot with the primary antibody, and, if required, secondary antibody and developing solution to visualize the detectable moiety, requires several steps of addition, incubation and washing, spread out over several hours. Automation of the Western blot development steps would advantageously reduce time and labor for processing samples. However, automation of Western blotting presents unique challenges, due to the nature of the reagents used. Specifically, proteins such as antibodies are susceptible to degradation and are therefore generally kept in a cold solution until they are ready for use. Further, antibodies are generally expensive, and, in many cases are in limited supply. Thus, it is desirable to avoid using a larger volume of solution, requiring larger volumes of antibody, in developing a Western blot. There is thus a need for a system that can reduce the need for manual manipulation of the Western blot, and that minimizes reagent waste.

SUMMARY OF THE INVENTION

In one embodiment, the invention comprises an automated developer for immuno-stained biological samples. The automated developer comprises a platform with a surface configured to receive an incubation box, a tower coupled to the platform surface, and an incubation box comprising a housing and a lid. The incubation box comprises a drain port and at least one entry port positioned to allow entry of a reagent into the interior of the incubation box. At least one syringe holder is provided, coupled to the tower and configured to receive a syringe, the syringe configured to hold a reagent within the syringe barrel, wherein the syringe holder is positioned to hold the syringe relative to the entry port in order to allow delivery of the reagent from within the syringe, through the entry port, into the incubation box. Also provided is a temperature control device configured to control the temperature of the reagent within the syringe, a motorized syringe pusher configured to mechanically force the reagent from within the syringe barrel, through the entry port into the incubation box, and a stirrer configured to agitate the reagent within the syringe. A processor is configured to control one or more of the motorized syringe pusher, the stirrer, and the temperature control device.

In another embodiment, an automated method of processing an immuno-stained biological sample comprises providing at least a primary antibody in a syringe, placing an undeveloped sample into an incubation box, contacting the undeveloped sample with the primary antibody by automatically activating a first motorized pusher to mechanically force the primary antibody from within the syringe barrel into the incubation box, automatically removing the primary antibody from within the incubation box after the contacting step, automatically pumping a wash buffer into the incubation box, and automatically removing the wash buffer from the incubation box.

In another embodiment, an automated developer for immuno-stained biological samples comprises a processor controlled rocking platform, a processor controlled syringe pusher and a processor controlled buffer pump. The processor is configured to control addition of antibody reagent to an incubation box by controlling the syringe pusher, and is configured to control addition of buffer the incubation box by controlling the buffer pump. The processor may be coupled to a user interface for programming operational timing of the syringe pusher and buffer pump.

BRIEF DESCRIPTION OF THE DRAWINGS

FIG. 4A is a sectional view of a syringe housing and syringes of one embodiment of the system disclosed herein.

FIG. 4B is a cutaway view of the syringe housing shown in FIG. 4A, showing the syringe housing, syringe, and magnetic stirrer of one embodiment of the system disclosed herein.

DETAILED DESCRIPTION OF THE PREFERRED EMBODIMENT

The embodiments disclosed herein relate to systems and methods for reducing the amount of manual manipulation required for blotting techniques used in molecular biology, while preserving reagents and minimizing waste.

Embodiments will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments disclosed herein. Furthermore, embodiments disclosed herein may include several novel features, no single one of which is solely responsible for its desirable attributes or which is essential to the embodiments herein described.

Figure 1:
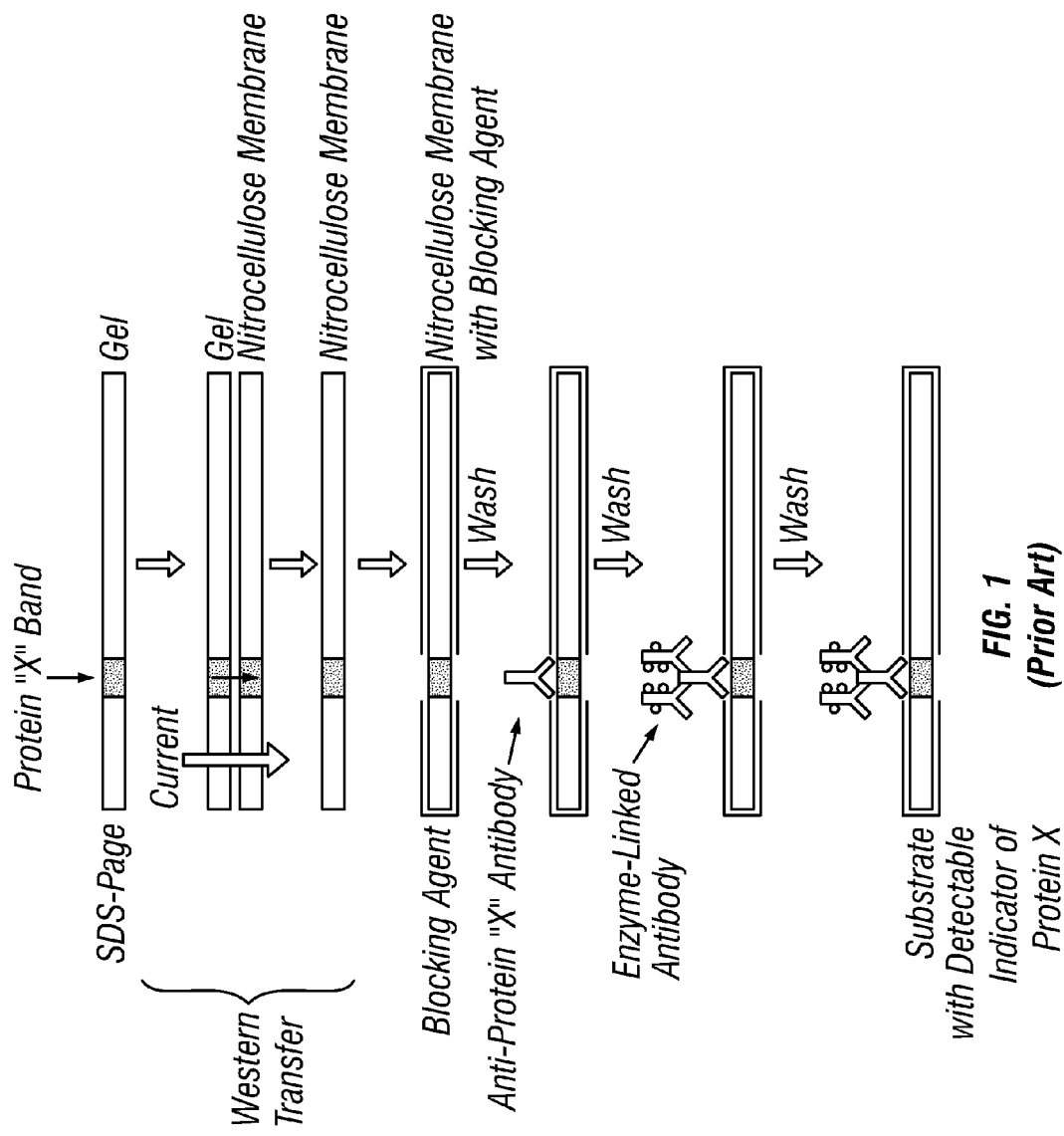
FIG. 1 depicts the steps of a "two-step" Western blotting approach.
Figure 2:
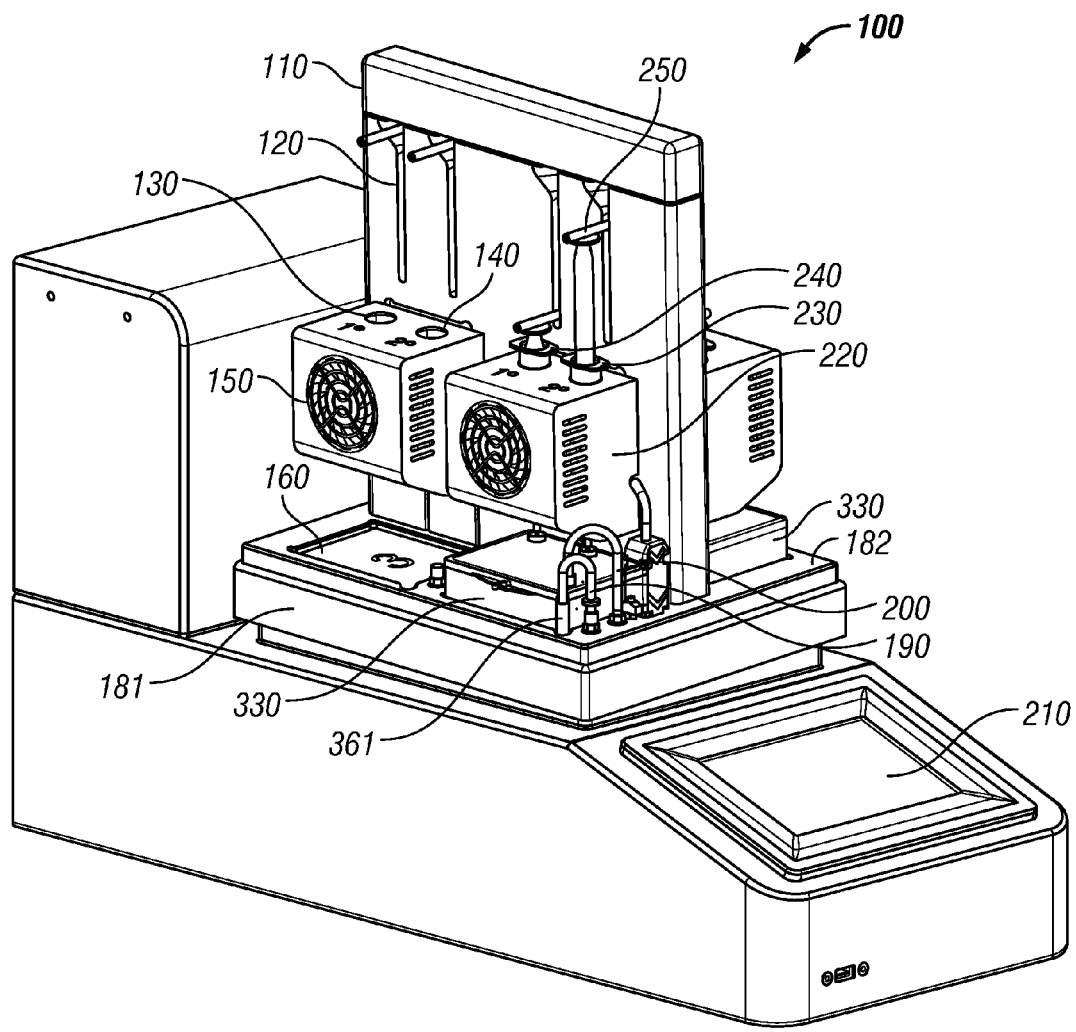
FIG. 2 is a perspective view of one embodiment of an automated blot processor.

Referring now to FIG. 2, a perspective view of an automated developer 100 according to one embodiment is shown. The automated developer 100 includes a platform 181 configured to receive one or more incubation boxes 330. In some embodiments, the incubation box 330 can be integral to the platform 181. In other embodiments, the incubation box 330 is separate from and can be removed from and replaced onto the platform 181. In some embodiments, the platform 181 is configured to agitate the incubation box. For example, in some embodiments, the platform 181 can be a rocking platform configured to tilt the incubation box 330 and its contents to various angles. This can be accomplished in a variety of manners, such as risers on the underside of the platform that are coupled to rotating cam shafts, eccentrically mounted bearings, or the like. A motor can turn the cam shafts, producing the rocking motion. In some embodiments, the platform 181 is designed to tilt the contents of the incubation box 330 in more than one plane. In some embodiments, the tilt angle and the speed of the rocking platform can be adjusted. In some embodiments, the tilt and speed parameters for the rocking platform can be adjusted manually. In some embodiments, the tilt and speed parameters of the platform can be controlled by a processor (designated 620 in FIG. 6) within the automated developer 100. In some embodiments, the processor includes a display and a user input interface, such as a touch screen 210. It will be appreciated that keypads, LED indicators, etc. could alternatively be used, although the touch screen display/user input interface is user friendly and flexible to allow for programming the actions of the developer as described further below.

In some embodiments, the surface 182 of the platform 181 includes a depression 160, configured to fit the incubation box 330 within the depression 160 to hold the incubation box 330 in place. In some embodiments, the incubation box can be configured to be locked onto the surface 182 of the platform, e.g., by a snap-lock mechanism or the like. The embodiment of FIG. 2 illustrates a platform with locations for accepting four incubation boxes 330.

In some embodiments, the automated blot processor includes a tower 110 attached to the platform surface 182. Tower 110 is configured to move with the platform 181, e.g., a rocking platform. The tower 110 can include one or more syringe holders 220, as described further below. The tower 110 can also include one or more channels 120, which hold pusher arms 250, as described below.

Figure 3C:
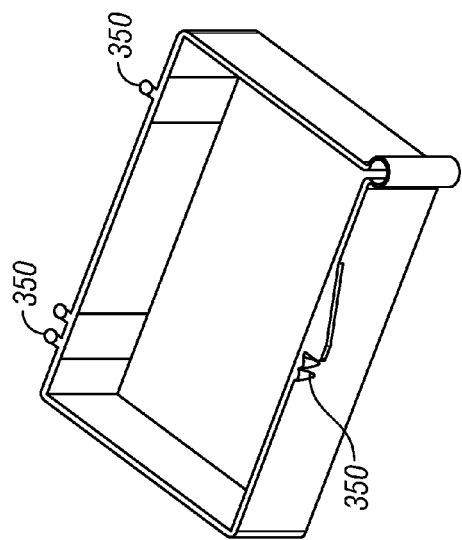
FIG. 3C is a perspective view of the incubation box shown in FIG. 4A.
Figure 3D:
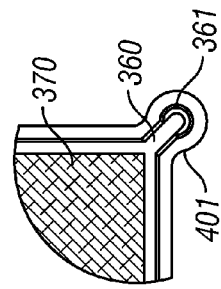
FIG. 3D is a planar view of one corner of an incubation box containing a membrane, and showing a drain channel.
Figure 3A:
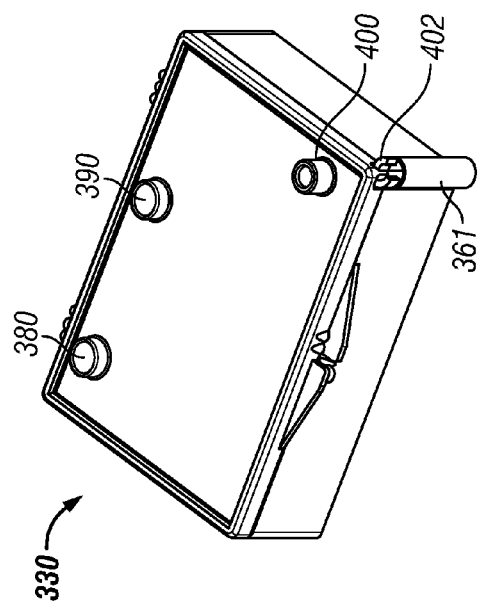
FIG. 3A is a perspective view of one embodiment of an incubation box, and an incubation box lid.
Figure 3B:
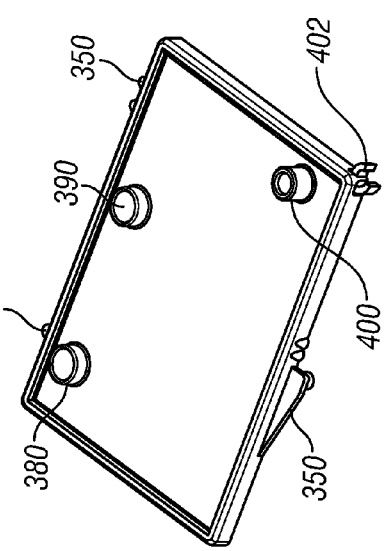
FIG. 3B is a perspective view of the incubation box lid shown in FIG. 4A.

Turning to FIG. 3A, a perspective view of an exemplary incubation box 330 is shown. The incubation box includes an incubation box housing and a lid. Perspective views of the incubation box housing and the lid are shown in FIGS. 3B and 3C, respectively. The incubation box housing can be configured to hold a filter or membrane 370, e.g., for a blot, and reagents, solutions, and the like, for incubation of the filter or membrane 370 during various stages of the blotting procedure. Preferably, the incubation box 330 is rectangular, although the skilled artisan will recognize that the shape of the incubation box 330 can be altered, so long as it is suitable for holding a membrane 370 and regents, solutions and the like. In some embodiments, the bottom inner surface of the blot housing includes a drain channel 360. In embodiments wherein the incubation box is rectangular, a drain channel can be located in one or more corners of the bottom inner surface of the blot housing.

The incubation box lid is configured to fit on top of the incubation box housing. The lid can be removably attached to the box housing, e.g., through a hinge and snap lock 350, or the like, that allows open and closing of the lid onto the incubation box housing. In some embodiments, the lid is not attached or coupled to the box housing but rather comprises a lip that is complementary to and fits around the outside of the box housing, keeping the lid in place on the box housing similar to a typical shoe box.

In some embodiments, the incubation box 330 can be disposable, and configured for single use. In some embodiments, the incubation box 330 can be made of reusable material.

As shown in FIG. 3B, the incubation box lid can have one or more entry ports, (e.g., one, two, three, four, or more entry ports), each configured to allow entry of reagents and solutions from a reagent source or a syringe into the interior of the incubation box housing. In FIG. 3B, the lid includes primary antibody entry port 380, a secondary antibody entry port 390, and a wash buffer entry port 400.

As shown in FIG. 3D, the incubation box housing 180 includes a drain feature 401, which allows for removal of reagents and buffers from within the incubation box housing. In some embodiments, the drain feature 361 includes a drain channel 360 leading into the waste port 361. In some embodiments, the waste port 361 is coupled to drain tubing 190. Various types of tubing known to those skilled in the art can be used in the embodiments disclosed herein including, but not limited to, bioperene thermoplastic elastomer tubing (Watson Marlow Bredel Products, Wilmington, Mass.), CHEM-DURANCET™ chemical pump tubing (COLE PARMER®, Vernon Hills, Ill.), and the like. In some embodiments, the tubing is secured to the waste port 361 by a tubing clamp 402. In some embodiments, the tubing is maintained in place in the waste port by frictional forces. In some embodiments, the tubing is maintained in place by a combination of, for example, a clamp and frictional forces. As shown also in FIG. 2, the drain tubing 190 enters the waste port from above and extends down to the drain channel located just off one bottom corner of the incubation box. The tubing 190 can lead to a waste container. In some embodiments, the tubing secured to the waste port 361 is coupled to a pump, such as a peristaltic pump, a piston pump, a hydraulic pump, or the like, via drain tubing 190. In preferred embodiments, the pump is a peristaltic pump. The pump can be used to cause the flow of reagents and solutions out the waste port 361, up into the drain tubing 190, and out of the incubation box.

It has been found advantageous to form the waste port 361 where the drain tube 190 attaches to the incubation box as an external feature of the rectangular perimeter of the remainder of the incubation box. Although it is possible to construct the system such that the drain tube merely enters the main portion of the incubation box from the top through the lid, the suction of the drain tube can pull the blot paper against the end of the drain tubing 190 and prevent good drainage from the box. In the embodiment of FIGS. 2 and 3, the blot paper cannot come into contact with the end of the drain tube 190. Furthermore, the drain channel 360 can include a downward draft angle, which advantageously allows for solutions and reagents to flow towards the waste port 361 where the end of the drain tubing 190 is located, while at the same time avoiding flotation of the blot toward the waste port 361 because the corner of the blot paper will rest in the corner of the main portion of the incubation box, and will not come into contact with the end of the drain tubing 190.

In some embodiments, the incubation box lid contains an entry port for a buffer source. In some embodiments, the buffer source can be coupled to the entry port via tubing. In some embodiments, the tubing can be connected to a pump, configured to force a buffer or solution through the tubing into the box housing. For example, in some embodiments, wash buffers, and the like used in Western blots can be delivered to the entry port via tubing 200 that is connected, e.g., via a peristaltic pump.

Turning now to FIG. 2, FIG. 3 and FIG. 4, in some embodiments, the reagent entry port(s) 380, 390 of the incubation box lid are positioned below syringes 230, 240, which are secured within syringe holders 130, 140 in a syringe housing 220 of the automated developer 100. For example, in some embodiments, a syringe 230, 240 can be filled with a reagent, and the entry ports 380, 390 can be positioned in line with each syringe tip 300 from which the reagent exits the syringe barrel 270, such that the reagent exits the syringe and passes through the entry port 380, 390 into the interior of the incubation box 330. As described further below, the contents of the syringe can be automatically added to the incubation box at the appropriate time by controlling a syringe pusher arm 250.

Automated delivery of reagents with the syringes shown in FIGS. 2 and 4 has a large advantage over the use of pump reagent delivery. Reagents, and in particular antibodies, are generally expensive, and in limited supply. The use of syringes 230, 240 as a reagent source advantageously eliminates dead volume, thereby reducing waste of valuable reagents. When the syringe plunger 260 is driven downward into the syringe barrel 231, the reagent is expelled from the syringe body with little to no waste. Those skilled in the art will appreciate that any syringe suitable for the purposes of the methods described herein can be used. In some embodiments, the syringe can be a 1 cc syringe, a 5 cc syringe, a 10 cc syringe, a 20 cc syringe, a 25 cc syringe, or the like.

FIG. 4 shows an example of a syringe housing 220 in more detail. FIG. 4A is plan view of the syringe housing. Temperature sensitive reagents that are susceptible to degradation are preferably kept at cooler temperatures until use. The features of the syringe housing described herein overcome the challenge of having to manually thaw and add reagents such as antibodies to an immuno-staining procedure such as a Western blot. In some embodiments, the syringe housing includes a temperature control feature, that cools (or possibly heats) the reagents as required. This feature advantageously eliminates the requirement of thawing and manually adding reagents, such as antibodies, just prior to use. Due to the fact that the reagents can be kept cool and do not need to be thawed and added throughout the procedure, the automation of the sequential incubation and washing steps of the procedure is enhanced.

Accordingly, in some embodiments, the syringe housing can also include a temperature control device positioned relative to the syringe to be able to control the temperature of the reagent within the syringe. In some embodiments, the temperature control device is a cooler, such as a ventilated Peltier junction thermoelectric cooler, a fan, and a refrigerated jacket that surrounds the syringe, or the like. In some embodiments, the temperature control device can also heat the reagents. In some embodiments, the temperature control device can be controlled by the processor. In some embodiments, the syringe housing includes a temperature control device that keeps the reagents within the syringes 230, 240, at −10° C., −5° C., 0° C., 4° C., 10° C., 25° C., or the like, during the developing process. A temperature sensor (630, FIG. 6) such as a thermocouple or thermistor is advantageously provided for feedback to the control processor so that programmable temperature regulation can be performed.

Shown in FIG. 4A is a syringe housing that includes a fan 150 and peltier cooler 320, that function to keep the reagents, e.g., antibodies and the like, cool during the blot process, in order to avoid degradation of the reagents. For example, in some embodiments, the fan and peltier cooler can be configured to keep reagents within the syringes 230, 240 between about 0° C. to about 10° C.

In some embodiments, the syringe housing 220 can include two openings 130, 140, to hold two syringes 230, 240, configured to house two different reagents, e.g., a primary antibody and a secondary antibody, respectively. The skilled artisan will appreciate that the syringe housings can be configured to hold one, two, three, four, five, six, seven, eight, nine, ten, or more syringes, depending upon the application. For example, in some embodiments, a primary antibody with a detectable label incorporated therein can be used in a Western blot, thereby eliminating the need for a secondary antibody. Accordingly, in some embodiments, the syringe housing 220 of the automated blot processor 100 can include one syringe opening 130, configured to receive one syringe 230.

FIG. 4B is a cutaway view of the syringe housing shown in FIG. 4A. A peltier cooler 320 can be positioned between the fan 150 and the syringe 240. The syringe fits within the syringe opening 130 and is inserted into a temperature controlled jacket 408. The Peltier cooler 320 draws heat from this jacket to heat sink 314 which is cooled by the fan 150. The plunger 260 is shown within the syringe barrel 231. In the embodiment of FIGS. 2 and 4, a single jacket 408, Peltier cooler 320, and fan 150 are used to control the temperature of two syringes. It will be appreciated that separate temperature control for each of multiple syringes can also be performed.

In some embodiments, a magnetic disc 290 or stirrer can be disposed within the reagent source, e.g., a syringe barrel 231, in order to agitate the reagent. As shown in FIG. 3B, the syringe housing 220 can include device for introducing a magnetic field to rotate or move the magnetic disc or stirrer 290, such as a solenoid coil 310, an electromagnet, a permanent magnet, or the like. In preferred embodiments, the device is a magnetic disc 290 that can lay flat in the bottom of the syringe barrel 231 when the solution is not being agitated, displacing as much reagent as possible out of the syringe when the plunger is depressed. In some embodiments, the processor is used to control the magnetic disc 290 or stirrer at pre-programmed time intervals via an electromagnet or solenoid coil 310, although it will be appreciated that in some embodiments the stirrer can be rotated continuously. Control of the stirring at pre-determined time intervals by the processor is advantageous in that it minimizes the heat generated by the stirrer, and thus reduces the risk of overheating reagents that are at risk of becoming denatured in excess heat. By way of example, the solenoid coil 310 can be energized with a biphasic voltage waveform with an amplitude and frequency adjusted to achieve optimal rotation of the disc or stirrer 290. Other means for stirring or agitating the reagent can be used, including but not limited to a physical stirrer, a device to deliver ultrasonic vibrations to the reagent source, or the like. As with the magnetic stirrer, such the alternative means for stirring can also be controlled by the processor.

Turning back to FIG. 2, in some embodiments, the automated blot processor 100 can include a motorized pusher that is configured to push the syringe plunger 260 down into the syringe barrel 231, expelling the contents in the barrel out of the syringe 230, 240, and through the entry port 380, 390. In some embodiments, the pusher can comprise an arm 250 that extends out of a channel 120 in the tower and is aligned along the travel path of the syringe plunger 260. The arm is configured to be automatically moved up or down along the height of the tower 110, thereby forcing the plunger 260 into syringe barrel 231 via downward travel at the appropriate programmed times. In some embodiments, the channel is angled the end of the channel that is distal to the platform (the "top" of the channel). The angle at the top of the channel 120 accommodates the pusher arm 250 in a position that is not directly above the syringe while the syringe is being loaded or unloaded into the syringe openings 130, 140.

Figure 5B:
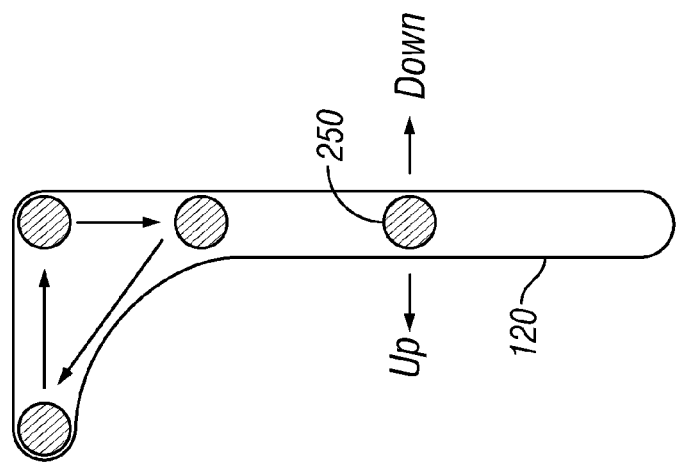
FIG. 5B illustrates motion of the syringe pusher within a guide channel of the automated developer.
Figure 5A:
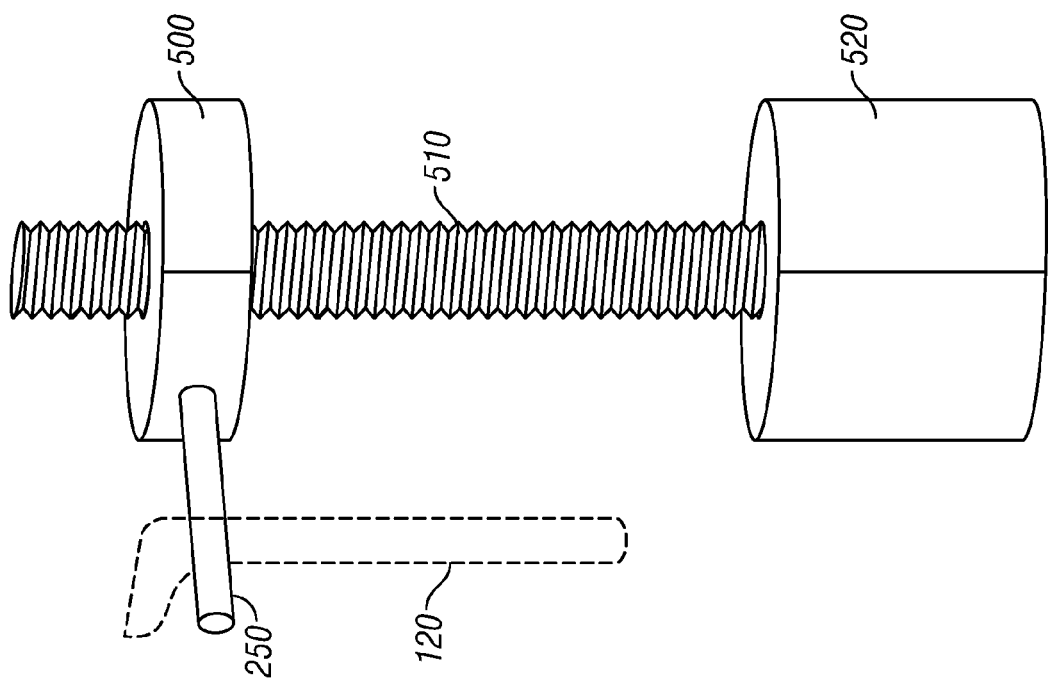
FIG. 5A is a perspective view of one embodiment of a syringe pushing mechanism.

In some embodiments, the pusher arm 250 is coupled to an internally threaded riser attached to an externally threaded shaft driven by a motor. This is illustrated in FIGS. 5A and 5B, which shows one embodiment for mechanically controlling a pusher arm 250. In this embodiment, an internally threaded riser 500 and externally threaded shaft 510 can be located within the tower, with the pusher arm 250 extending out of the channel 120. The motor 520 can rotate the externally threaded shaft 510 within the internally threaded riser 500. The pusher arm is forced against the walls defining the channel 120, which prevents rotation of the riser, and instead causes the riser to move up and down the shaft, depending upon which way the motor turns the shaft.

In some embodiments, the processor controls the motor that moves the pusher arm 250 up and down the channel 120 of the tower 110. As the arm moves down the channel 120 in the tower 110 it forces the syringe plunger 260 into the syringe barrel 231. The processor may then reverse the direction of the motor, in order to move the pusher arm 250 back up the channel 120 after the contents of the syringe 230, 240 have been expelled from the syringe barrel 231 into the incubation box housing 180. In some embodiments, when the arm 250 travels back up the channel 1210, rotation of the motorized shaft automatically moves the pusher arm into the angled portion of the channel, so that the syringe 230, 240 can be easily removed. This is illustrated in FIG. 5B, where motor rotation pushes the arm 250 against the left channel wall when the riser is moving up, and against the right channel wall when the riser is moving down. When the arm 250 moves up into the upper angled portion of the channel 120, motor rotation will keep the arm 250 against the left wall, and move the arm away from being directly above the syringe. When the arm is moved down again, motor rotation first pushes the arm 250 against the right channel wall, and then the arm moves down into the lower portion of the channel 120.

In some embodiments, the automated developer is connected to one or more buffer sources via tubing 200. In some embodiments, a pump, such as a peristaltic pump controls the movement of buffer from the buffer source, into the tubing. In some embodiments, the tubing is attached using any connector known in the art and suitable for the embodiments disclosed herein, e.g., a luer lock, to an entry port on the incubation box lid.

Figure 6:
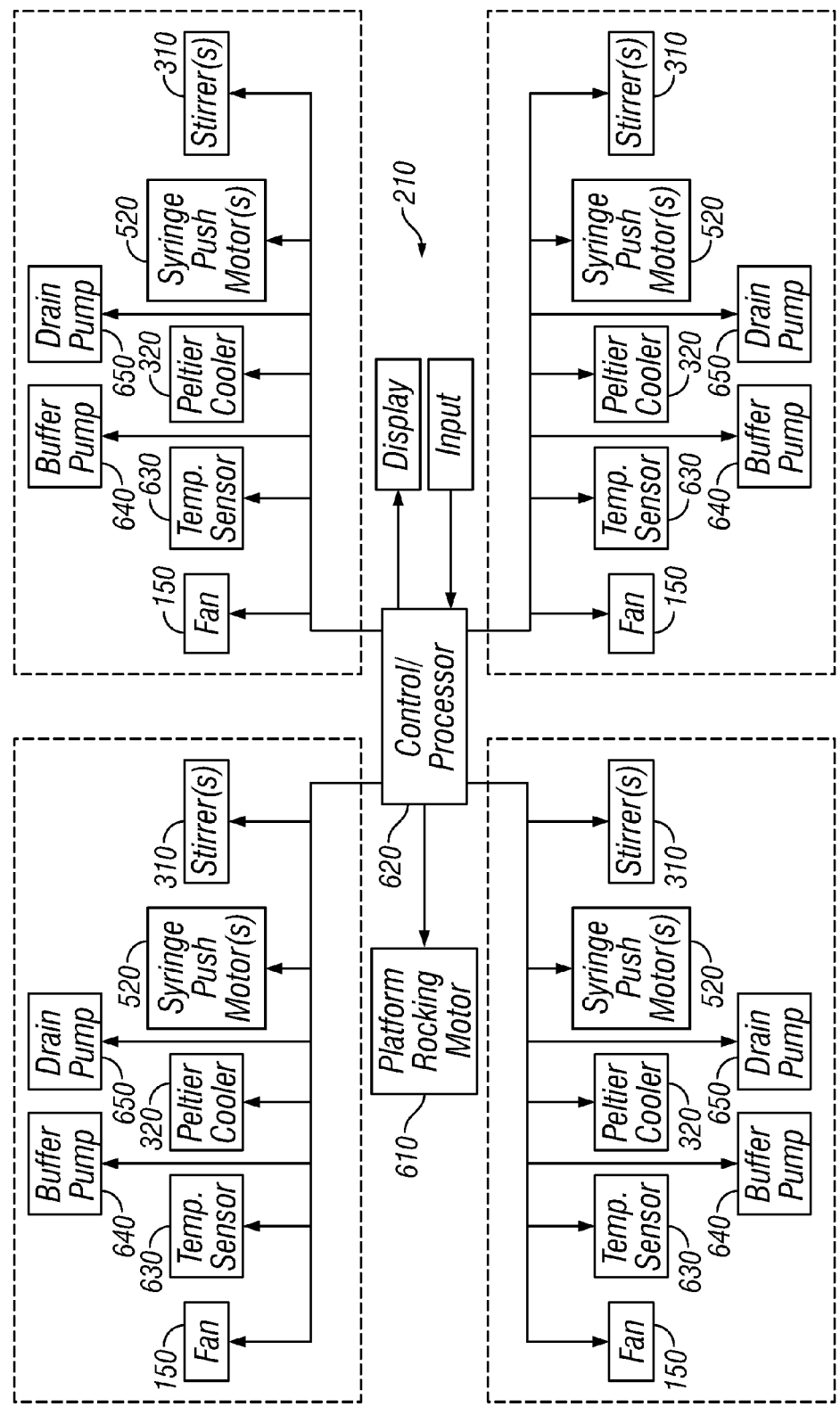
FIG. 6 is a block diagram of the components of one embodiment of an automated developer.

FIG. 6 is a block diagram of the components of the developer of FIG. 2 illustrating the automation control paths in this embodiment. The developer may include some control and processing circuitry 620 which may be programmable through a user input device. The control circuitry 620 controls a motor driving the rocking platform. Also, the control circuitry can separately control four reagent and buffer input/drain stations as are shown in FIG. 2. With this configuration, separate reagent and buffer addition and removal schedules can be programmed into the developer. In some cases, it is convenient to program the processing cycles for different incubation boxes so that they end at the same time, even if they have different schedules for adding reagents. To synchronize the completion time, it is possible to extend, for example, one or more wash periods for those incubation boxes that have early reagent addition and removal schedules. Generally, one or more of the wash or buffer cycles can be extended without affecting the immuno-stain development. This feature frees the scientist and technician from a large amount of otherwise manual monitoring and development steps which quickly expand to a burdensome number when different immuno-stain development procedures have some different desired incubation times for some of the steps.

It will be appreciated that the processor element of the automated developer 100 may be integral to the housing of the developer itself, or all or part of the processing and control circuits can be separate from the developer itself. In some embodiments, the processor can be a specialized microcontroller which is designed specifically for controlling the elements of the automated developer device. Alternatively, the processor can be a standard personal computer device such as an Intel processor-based PC running an off the shelf operating system such as Windows, Linux, MacOS, or the like. As used herein, the term "processor" generally refers to one or more logic and control circuits which are connected to the automated developer 100 to control the operation of various components of the automated developer as described herein. In some embodiments, the processor can include direct hardware interface such as a USB port, an RS232 interface, and IP network interface (wired or wireless), or some other type of connection, to load software to control the components and functions of the automated blot processor. In some embodiments, the processor is integrated into the automated developer, which then interfaces with a touch-screen user interface 210, that enables the user to set the parameters for automated control of the different components of the automated developer.

In some embodiments, the processor can include software that allows the user to enter the timing and parameters for controlling one or more components of the developer 100, such as the motorized pusher, the rocking platform, the temperature control, the peristaltic pump(s), and the like. In some embodiments, the software allows the user to program the developer to complete a Western blotting procedure, including controlling the following: the addition of reagents, such as blocking buffer, wash buffer, primary and secondary antibodies, and the like to the incubation box at predetermined times; the rocking of the platform; the drainage of buffers and reagents from within the incubation box; stirring of reagents within the syringes; controlling the temperature of the reagents; and the like. In some embodiments, the processor can allow for automated collection of "run data" including, for example, temperature and volume measurements, reagent volume and incubation time, operator identity, date and time, etc.

In embodiments wherein the automated developer includes more than one syringe holder 220, and more than one incubation box 330, the processor can be set to add and remove reagents to each different incubation box 330, enabling individual Western blots that require different incubation times with different reagents to be processed at the same time.

Some embodiments provide a method of processing a Western blot, using the automated developer 100 described herein. In some embodiments, a user will manually aspirate reagents such as a primary antibody, into a syringe, and place the syringe in the syringe holder. In some embodiments, the Western blot procedure includes an incubation step with a secondary antibody if the primary antibody is not labeled with a detectable label. In such embodiments, the user can aspirate the secondary antibody reagent into a second syringe, and place the second syringe within the syringe holder.

The user can place one end of a buffer line into a buffer source. In some embodiments, there is more than one buffer line, each connected to a different buffer source. For example, the user can place a first buffer line into a first buffer source containing blocking buffer and a second buffer line into a second buffer source containing wash buffer.

The user can place a filter onto which proteins have been transferred into the incubation box housing, and placing the housing lid onto the incubation box. The user can then set the automated developer to perform the steps of: contacting the undeveloped blot in the incubation box with the primary antibody by activating the first motorized pusher to mechanically force the primary antibody from within the first syringe; agitating, e.g., by rocking the incubation box for a period of time; draining the primary antibody from the incubation box; pumping a wash buffer from a buffer source into the interior of the incubation box; rocking the incubation box for a period of time; removing the wash buffer from the incubation box; contacting the blot with the secondary antibody by activating the second motorized pusher to mechanically force the secondary antibody from within the second syringe; and removing the secondary antibody from within the incubation box.

The above described blot processor has many significant advantages. Automating the dispensing of antibodies from syringes eliminates a significant amount of waste that would occur if the antibodies were pumped into the incubation box with a pump and tubing system. Antibody solutions in the syringes can be temperature controlled and automatically stirred. Separate control of multiple development processes simultaneously is also provided.

It will further be appreciated that blots are not the only biological samples that can be developed using the above described automated developer. It is often desirable to stain tissue slices with antibodies to produce visual indications of the presence or absence of different types of proteins, DNA or other biological molecules in a given sample of tissue. This staining procedure also involves the application of buffers and antibodies to the tissue samples for selected incubation times and these procedures can also be automated with the automated developer described herein. In some cases, the tissue samples are relatively small, and the incubation box described above can be segmented with mesh walls that allow the solutions to pass through but maintain separate tissue samples in separate portions of the incubation box.

The above-described embodiments have been provided by way of example, and the present invention is not limited to these examples. Multiple variations and modifications to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments.

What is claimed is:

1. An automated developer for immuno-stained biological samples, comprising:
    a platform with a surface configured to receive an incubation box, wherein the platform is a rocking platform;
    a processor configured to control the duration and/or intensity of the rocking of the platform;
    a tower coupled to the platform surface;
    at least one incubation box comprising a housing and a lid, wherein said incubation box comprises at least one waste port, and at least one entry port positioned to allow entry of a reagent into the interior of the incubation box;
    at least one syringe holder coupled to the tower and configured to receive a syringe, said syringe configured to hold the reagent within the syringe barrel, wherein the syringe holder is positioned to hold the syringe relative to the entry port in order to allow delivery of the reagent from within the syringe, through the entry port, into the incubation box;
    a temperature control device configured to control the temperature of the reagent within the syringe;
    a motorized syringe pusher configured to mechanically force the reagent from within the syringe barrel, through the entry port into the incubation box;
    a stirrer configured to agitate the reagent within the syringe; and
    a processor configured to control one or more of the motorized syringe pusher, the stirrer, and the temperature control device.

2. The automated developer of claim 1, wherein the lid comprises a first and a second reagent entry port.

3. The automated developer of claim 2, comprising two syringe holders configured to receive a first and a second syringe, wherein the first and second syringes are configured to hold a first and a second reagent within the syringe barrel of the first and second syringe, respectively, and a first and second motorized pusher, configured to mechanically force the reagent from the first and second syringe barrels, respectively, wherein the syringe holder is positioned to hold the first and the second syringe relative to the first and the second entry port in order to allow transfer of the first and the second reagents from within the first and the second syringes, through the first and the second entry ports, respectively.

4. The automated developer of claim 2, further comprising a buffer source, configured to hold a buffer.

5. The automated developer of claim 4, wherein the housing lid further comprises a third entry port through which buffer from the buffer source enters into the interior of the incubation box.

6. The automated developer of claim 5, wherein the buffer source is connected to a pump.

7. The automated developer of claim 1, wherein the waste port is connected to a peristaltic pump through a tubing.

8. The automated developer of claim 1, wherein the platform is configured to receive a plurality of incubation boxes.

9. The automated developer of claim 1, wherein the stirrer is a magnetic disc located within the syringe barrel.

10. The automated developer of claim 9, further comprising a solenoid coil positioned relative to the reagent source to allow the solenoid coil to control movement of the magnetic disc.

11. The automated developer of claim 1, wherein said incubation box is rectangular, and wherein said drain channel is located external to said rectangle and adjacent to one of the corners of the rectangle.

12. The automated developer of claim 1, wherein the rocking platform is configured to position the incubation box at an angle, wherein the angle allows the reagent or the buffer within the incubation box to drain through the drain channel into the waste port.

13. The automated developer of claim 1, wherein the processor controls the addition of the reagent into the incubation box, and removal of the reagent through the drain channel at predetermined times.

14. The automated developer of claim 1, wherein the processor controls the addition of the wash buffer into the incubation box, and removal of the wash buffer through the drain channel at predetermined times.

15. The automated developer of claim 14, wherein the processor is programmable to add a predetermined amount of the reagent source into the incubation box.

16. The automated developer of claim 1, wherein the temperature control device comprises a ventilated peltier junction cooler.

17. The automated developer of claim 16, wherein the ventilated peltier junction cooler is located within the syringe housing.

18. The automated developer of claim 1, further comprising:
   a channel, wherein the channel comprises a vertical portion running parallel to the length of the tower, and an angled portion at the top of the vertical portion;
   a pusher arm configured to push the syringe barrel into the syringe;
   an internally threaded riser within the tower, wherein the pusher arm is coupled to the internally threaded riser, and wherein the pusher arm extends through the channel from within the tower to the exterior of the tower;
   an externally threaded shaft to which the internally threaded riser is coupled, wherein said externally threaded shaft is coupled to and rotated by a motor.

19. An automated developer for immuno-stained biological samples, comprising:
   a platform with a surface configured to receive an incubation box, wherein the platform is a rocking platform;
   a processor configured to control the duration and/or intensity of the rocking of the platform;
   a tower coupled to the platform surface;
   a incubation box comprising an incubation box housing and a lid, wherein said incubation box housing comprises a drain means, configured to drain reagents and buffers from within the incubation box housing;
   at least one syringe holder configured to receive a syringe, said syringe configured to hold the reagent within the syringe barrel, wherein the syringe holder is positioned to hold the syringe relative to the entry port in order to allow delivery of the reagent from within the syringe, through the entry port, into the incubation box, wherein said syringe holder is coupled to the tower;
   a temperature controlling means, configured to control the temperature of the reagent within the syringe;
   a motorized syringe pusher configured to mechanically force the reagent from within the syringe barrel, through the entry port into the incubation box;
   an agitation means, configured to agitate or stir the reagent within the syringe; and
   a means for automatically controlling one or more of the motorized syringe pusher, the agitating means, and the temperature control means.

* * * * *